(12) United States Patent
Kim et al.

(10) Patent No.: US 6,380,359 B1
(45) Date of Patent: Apr. 30, 2002

(54) LIPOSOMES COMPRISING PEPTIDE ANTIGENS DERIVED FROM X PROTEIN OF HEPATITIS B VIRUS

(75) Inventors: Tae-Yeon Kim; Ki-Young Lee, both of Kyonggi-Do; Jin-Soo Chang, Seoul; Sung-Yoo Cho, Kyonggi-Do; Yu-Kyeong Hwang, Kyonggi-Do; Myeong-Jun Choi, Kyonggi-Do; Hong-Seok Cheong, Kyonggi-Do, all of (KR)

(73) Assignee: Mogam Biotechnology Research Institute, Kyonggi-Do (KR)

( * ) Notice: Subject to any disclaimer, the term of this patent is extended or adjusted under 35 U.S.C. 154(b) by 0 days.

(21) Appl. No.: 09/051,006
(22) PCT Filed: Jan. 19, 1998
(86) PCT No.: PCT/KR98/00010
  § 371 Date: Mar. 30, 1998
  § 102(e) Date: Mar. 30, 1998
(87) PCT Pub. No.: WO99/36434
  PCT Pub. Date: Jul. 22, 1999

(30) Foreign Application Priority Data

Jan. 19, 1998 (KR) .............................. PCT/KR98/00010

(51) Int. Cl.$^7$ ................................................ C07K 1/00
(52) U.S. Cl. ..................... 530/350; 530/350; 530/300; 530/324; 514/12; 514/16; 514/53; 424/450; 424/400; 424/DIG. 8
(58) Field of Search ................................ 530/350, 300, 530/324; 424/450, 400, DIG. 8; 514/2, 16, 53

(56) References Cited

FOREIGN PATENT DOCUMENTS

| | | | |
|---|---|---|---|
| WO | WO85/03950 | * | 9/1985 |
| WO | WO93/03753 | * | 3/1993 |
| WO | WO94/20127 | * | 9/1994 |

OTHER PUBLICATIONS

W. I. White et al., "Antibody and Cytotoxic T-lymphocyte Responses to a Single Liposome–Assiciated Peptide Antigen", *Vaccine*, 13(12):1111–1122 (1995).

F. Zhou and L. Huang, Monophosphoryl Lipid A Enhances Specific CTL Induction by a Soluble Protein Antigen Entrapped in Liposomes, *Vaccine*, 11(11):1139–1144 (1993).

Barbara Rehermann et al., "Cytotoxic Lymphocyte Responsiveness after Resolution of Chronic Hepatitis B Virus Infection", *The Journal of Clinical Investigation*, 97(7): 1655–1665 (1996).

Ramin Nayersina et al., "HLA A2 Resitrcted Cytotoxic T Lymphocyte Responses to Multiple Hepatitis B Surface Antigen Epitopes during Hepatitis B Virus Infection", *The Journal of Immunology*, 150(10):4659–4671 (1993).

* cited by examiner

*Primary Examiner*—Karen Cochrane Carlson
*Assistant Examiner*—Hope A. Robinson
(74) *Attorney, Agent, or Firm*—Darby & Darby (57) ABSTRACT

The present invention relates to liposomes comprising novel peptide antigens which play a role in regulating human immunity against hepatitis B virus, more specifically, to peptide groups corresponding to epitopes of antigens derived from X protein of HBV which induce cytotoxic T lymphocytes against the virus or immunological tolerance to the virus, and pH-sensitive liposomes comprising said peptide groups to induce cellular immunity so that CTLs specific to the virus can be produced. Since peptide antigens derived from X protein such as X3, X4, X5, X6 and X7 activate CTL which can recognize HBV antigens present in human body, and can also be recognized by the CTL, the liposomes can be used for the development of proposed therapeutic agents for the prevention and treatment of HBV-associated diseases.

2 Claims, 3 Drawing Sheets

SEQUENCE LISTING

<160> NUMBER OF SEQ ID NOS: 10

<210> SEQ ID NO 1
<211> LENGTH: 9
<212> TYPE: PRT
<213> ORGANISM: Hepatitis B virus

<400> SEQUENCE: 1

His Leu Ser Leu Arg Gly Leu Phe Val
1               5

<210> SEQ ID NO 2
<211> LENGTH: 9
<212> TYPE: PRT
<213> ORGANISM: Hepatitis B virus

<400> SEQUENCE: 2

Val Leu His Lys Arg Thr Leu Gly Leu
1               5

<210> SEQ ID NO 3
<211> LENGTH: 9
<212> TYPE: PRT
<213> ORGANISM: Hepatitis B virus

<400> SEQUENCE: 3

Ala Met Ser Thr Thr Asp Leu Glu Ala
1               5

```
<210> SEQ ID NO 4
<211> LENGTH: 9
<212> TYPE: PRT
<213> ORGANISM: Hepatitis B virus

<400> SEQUENCE: 4

Cys Leu Phe Lys Asp Trp Glu Glu Leu
 1               5

<210> SEQ ID NO 5
<211> LENGTH: 9
<212> TYPE: PRT
<213> ORGANISM: Hepatitis B virus

<400> SEQUENCE: 5

Glu Ile Arg Leu Lys Val Phe Val Leu
 1               5

<210> SEQ ID NO 6
<211> LENGTH: 9
<212> TYPE: PRT
<213> ORGANISM: Hepatitis B virus

<400> SEQUENCE: 6

Val Leu Cys Leu Arg Pro Val Gly Ala
 1               5

<210> SEQ ID NO 7
<211> LENGTH: 9
<212> TYPE: PRT
<213> ORGANISM: Hepatitis B virus

<400> SEQUENCE: 7

Thr Leu Pro Ser Pro Ser Ser Ser Ala
 1               5

<210> SEQ ID NO 8
<211> LENGTH: 15
<212> TYPE: PRT
<213> ORGANISM: HIV

<400> SEQUENCE: 8

Arg Ile Gln Arg Gly Pro Gly Arg Ala Phe Val Thr Ile Gly Lys
 1               5                  10                  15

<210> SEQ ID NO 9
<211> LENGTH: 26
<212> TYPE: PRT
<213> ORGANISM: HIV

<400> SEQUENCE: 9

Thr Arg Pro Asn Asn Asn Thr Arg Lys Arg Ile Arg Ile Gln Arg Gly
 1               5                  10                  15

Pro Gly Arg Ala Phe Val Thr Ile Gly Lys
             20                  25

<210> SEQ ID NO 10
<211> LENGTH: 8
<212> TYPE: PRT
<213> ORGANISM: HCV

<400> SEQUENCE: 10

Asp Leu Met Gly Tyr Ile Pro Leu
 1               5
```

LIPOSOMES COMPRISING PEPTIDE ANTIGENS DERIVED FROM X PROTEIN OF HEPATITIS B VIRUS

BACKGROUND OF THE INVENTION

1. Field of the Invention

The present invention relates to liposomes comprising novel peptide antigens which play a role in regulating human immunity against hepatitis B virus("HBV"), more specifically, to peptide groups corresponding to epitopes of antigens derived from X protein of HBV which induce cytotoxic T lymphocytes("CTL") against the virus or immunological tolerance to the virus, and pH-sensitive liposomes comprising said peptide groups to induce cellular immunity so that CTLs specific to the virus can be produced.

2. Description of the Prior Art

When human body is infected with HBV, various physiological responses occurs to remove the virus. Among the responses, one of most important ones is to destroy and remove the infected cells, which finally results in recovery from viral infection. Destruction of the infected cells is accomplished by another kind of cell having cytotoxicity, which is called as CTL. To exhibit cytotoxicity, CTL has to, first of all, recognize some of peptides derived from invading viral proteins. In general, viral proteins are synthesized within the infected cells, and then, they are converted to short peptides consisting of 8 to 15 amino acids through intracellular degradation process. When some of the peptides thus produced appear at cell surface in a combined form with intracellular major histocompatibility complex molecule("MHC"), CTL recognizes them to destroy the infected cells. On the other hand, MHC is classified into Class I and Class II, and it has been known that MHC of Class I plays an important role in induction of CTL, compared with MHC of Class II. However, it has been reported that sites of protein(peptides) recognized by CTL are restricted to only ones having specific amino acid sequences among the peptides produced by degradation of viral proteins(see: Fremont, D. et al., Science, 257:919–926 (1992); Matsumura, M. et al., Science, 257:929–934(1992)).

Accordingly, finding of amino acid sequences of those specific sites permits chemical synthesis and production of peptides corresponding to the amino acid sequences, thus employment of the peptides allows artificial induction of CTL specifically recognizing hepatitis virus in human body or regulation of other immune responses such as immunosuppression, which results in effective prevention and treatment of diseases caused by the hepatitis virus.

Based on the knowledge, many researchers have made efforts to find amino acid sequences of peptides recognized by CTL among the peptides produced by degradation of hepatitis viral proteins. As a result, several specific amino acid sequences have been found, and it has been expected that several sequences would be further discovered. In addition, to employ such peptides in prevention and treatment of hepatitis-associated diseases, it is necessary that peptides as many as possible are used at the same time, and their effects may vary, depending on the kinds of peptides. Therefore, discovery of amino acid sequences of such peptides has very important significance.

Peptides for prevention and treatment of hepatitis B which have been reported to be recognized by CTL are mainly derived from S(surface antigen) protein and C(core) protein of HBV. However, peptides derived from X protein, one of antigenic proteins of HBV have not been reported so far, even though a series of studies using transgenic mice clearly revealed that X protein is directly involved in HBV-associated liver cancer(see: Hoyhne et al., EMBO J., 9:1137–1145(1990); Kim et al., Nature, 351:317–320 (1991)).

On the other hand, when phospholipids are dispersed in water, polar head groups are oriented to water and hydrophobic tails aggregate by hydrophobic interaction, spontaneously to form spherical closed vesicles of bilayer which are called as "liposomes". Such a liposome has been widely used as a carrier in drug delivery system as well as a modelling study of biological membrane(see: Lee, J. W. and Kim, H., Arch. Biochem. Biophys., 297:354(1992); Hahn, K. H. and Kim, H., J. Biochem., 110:635(1991); Yun, C. H. and Kim, H., J. Biochem., 105:406(1989); Kim, J. and Kim, H., Biochemistry, 25:7867(1986); Kim, J. and Kim, H., Korean Biochem. J., 18:403(1985)).

Recently, it has been reported that liposomes can be applied in the field of immunology, which accelerated studies on the liposomes as carriers of vaccines or adjuvants(see: Rooijen, N. V., Vaccine, 11:1170(1993)). In general, when liposomes are injected intravenously, they are easily captured by macrophage("MO") which is present abundantly in blood, which plays very important roles in processing of liposomal antigen as well as immunological processing of antigen.

Also, methods for inducing CTL response specific to a certain proteins or peptides employing pH-sensitive liposomes have been recently developed(see: Readdy, R. et al., J. Immunol. Methods, 141:157(1991); Zhou, F. et al., J. immunol. Methods, 145:143(1991); Nair, S. et al., J. Exp. Med., 175:609(1992); Harding, C. V. et al., J. Immunol. 147:2860(1991); Zhou, F. and Huang, L., Vaccine, 11:1139 (1993)), and pH-sensitive liposomes have been widely used as carriers and adjuvant systems of the protein or peptide antigen for the development of subunit vaccine. In this connection, the present inventors have reported a process for preparing a pH-sensitive liposome which permits selective transportation of anti-cancer drugs(see: Chol, M. J. et al., J. Biochem., 112:694(1992))

SUMMARY OF THE INVENTION

In accordance with the present invention, a series of peptides specifically recognized by CTL, among peptides derived from HBV X protein, are provided. And, pH-sensitive liposomes comprising the peptide antigens derived from HBV X protein are also provided. The present inventors found that the liposomes may be used for the development of proposed therapeutic agents for the prevention and treatment of HBV-associated diseases by inducing cellular immunity so that CTLs specific to she peptide antigens of HBV can be produced.

A primary object of the invention is, therefore, to provide peptide antigens derived from HBV X protein which can be recognized by CTL and show cytotoxicity to the virus.

The other object of the invention is to provide pH-sensitive liposomes comprising the said peptide antigens which can induce celluar immunity.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Based on a previous finding that peptides binding to MHC Class I molecules have specific amino acid sequences, peptides having potentials of binding to MHC Class I molecules were sequenced from the full amino acid sequences of HBV X protein. That is, since peptides which can bind to HLA-A2, a human MHC Class I molecule, have leucine, valine or isoleucine at C-terminus and second position from N-terminus(see: Matsumura, M. et al., Science, 257:929–934(1992)), amino acid sequences satisfying the said condition were screened from the full amino acid sequences of HBV X protein, and peptides having potentials of binding to HLA-A2 molecule, i.e., peptide antigens which can induce CTL response by binding to the human MHC Class I molecule, were selected, among peptides produced by degradation of HBV X antigenic protein, based on three-dimensional structure of the molecule(see: Table 1 below). Then, peptides were synthesized chemically according to the amino acid sequences thus determined. Amino acid sequences of peptides derived from HBV X protein, i.e., X3, X4, X5, X6 and X7, are disclosed in Table 1 below.

TABLE 1

Location and amino acid sequences of peptides recognized by CTL among peptides produced by degradation of HBV x protein

| Peptide | Position of amino acid sequence | Amino acid sequence* | Number of amino acid |
|---|---|---|---|
| x3 (SEQ ID NO: 1) | 052–060 | HLSLRGLFV | 9 |
| x4 (SEQ ID NO: 2) | 092–100 | VLHKRTLGL | 9 |
| x5 (SEQ ID NO: 3) | 102–110 | AMSTTDLEA | 9 |
| x6 (SEQ ID NO: 4) | 115–123 | CLFKDWEEL | 9 |
| x7 (SEQ ID NO: 5) | 126–134 | EIRLKVFVL | 9 |

*: Amino acid sequences are abbreviated according to the IUPAC-IBU nomenclature system.

The present invention covers not only peptides consisting of 9 amino acids described above but also peptides added with 1 to 5 amino acids to N- or C-terminus of the said peptides and their functional equivalents. In the present invention, the term 'functional equivalents' is employed to mean all peptides substituted by 1 or 2 amino acids among the amino acid sequences of the said peptides. For example, substitution comprises the combinations such as Gly, Ala; Val, Ile, Leu; Asp, Glu; Asn, Gln; Ser, Thr; Lys, Arg; and, Phe, Tyr.

In order to prepare pH-sensitive liposomes comprising the peptide antigens derived from HBV X protein, phosphatidylethanolamine-β-oleoyl-γ-palmitoyl(POPE) and cholesterol hemisuccinate(CHOH) are mixed in a molar ratio of 6:4 to 8:2, most preferably 7:3, or POPE, phosphatidylethanolamine(PE) and CHOH are mixed in a molar ratio of 3:3:4 to 4:4:2, most preferably 3.5:3.5:3, finally to form thin membrane of phospholipid. And then, the liposomes thus prepared are added to a buffer solution containing the said peptide antigens derived from HBV X protein. In this connection, liposomes comprising peptide antigens derived from HBV X protein are prepared by mixing 1 or more kinds of peptide antigen and phospholipid in a molar ratio of 1:5 to 1:25, most preferably 1:20. Also, the pH-sensitive liposomes prepared according to the present invention may further comprise up to 1 mole % monophosphoryl lipid A as a phospholipid.

The liposomes of the present invention encapsulate peptide antigens inducing human CTL response, and the pH-sensitive liposomes which are used as carriers of the peptides, can also induce CTL response specific to the virus from which the encapsulated peptides are derived. Naturally, it is clearly demonstrated that the pH-sensitive liposomes comprising the said peptides can induce human cellular immunity.

In describing amino acid sequences of the peptides of the invention, one-letter symbols abbreviated by the IUPAC-IUB standards are employed as followings:

| Amino acid | Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The present invention is further illustrated in the following examples, which should not be taken to limit the scope of the invention.

EXAMPLE 1

Determination of Peptides Having Potentials of Binding to MHC Molecules within X Protein Since peptides which can bind to HLA-A2, a human MHC Class I molecule, have leucine, valine or isoleucine at C-terminus and second position from N-terminus(see: Matsumura, M. et al., Science, 257:929–934(1992)), amino acid sequences satisfying the said condition were first screened from the full amino acid sequences of HBV X protein, and peptides having potentials of binding to HLA-A2 molecule were finally selected, considering three-dimensional structure of the molecule (see: Table 1 above) Then, chemical synthesis of the peptides were carried out by the method conventionally known in the art, based on the amino acid sequences thus determined.

EXAMPLE 2

Synthesis of Peptides and Determination of their Binding to MHC Molecules

Seven different peptides including the peptides as disclosed in Table 1 above which were derived from HBV X protein were synthesized chemically and dissolved in phosphate buffered saline(hereinafter, referred to as "PBS"). In order to investigate whether the peptides can bind to MHC Class I molecules associated with induction of CTL, each peptide was added to T2 cell line in a concentration of 100, 64, 32, 16, 8, 4, 2 and 1 μg/ml, respectively, and reacted at 37° C. for 4 hours. And then, the cells were washed with PBS to remove unreacted peptides, added with BB7.2 antibody against HLA-A2.1, a human MHC Class I molecule, and reacted at 4° C. for 1 hour. The cells were washed with PBS again, added with fluorescein isothiocyanate(FITC)-conjugated anti-mouse immunoglobulin antibody, and reacted at 4° C. for 1 hour. Then, fluorescence of the cells was determined using fluorocytometer(FACScan, BECTON DICKINSON) and the results were shown in FIG. 1.

Figure 1:
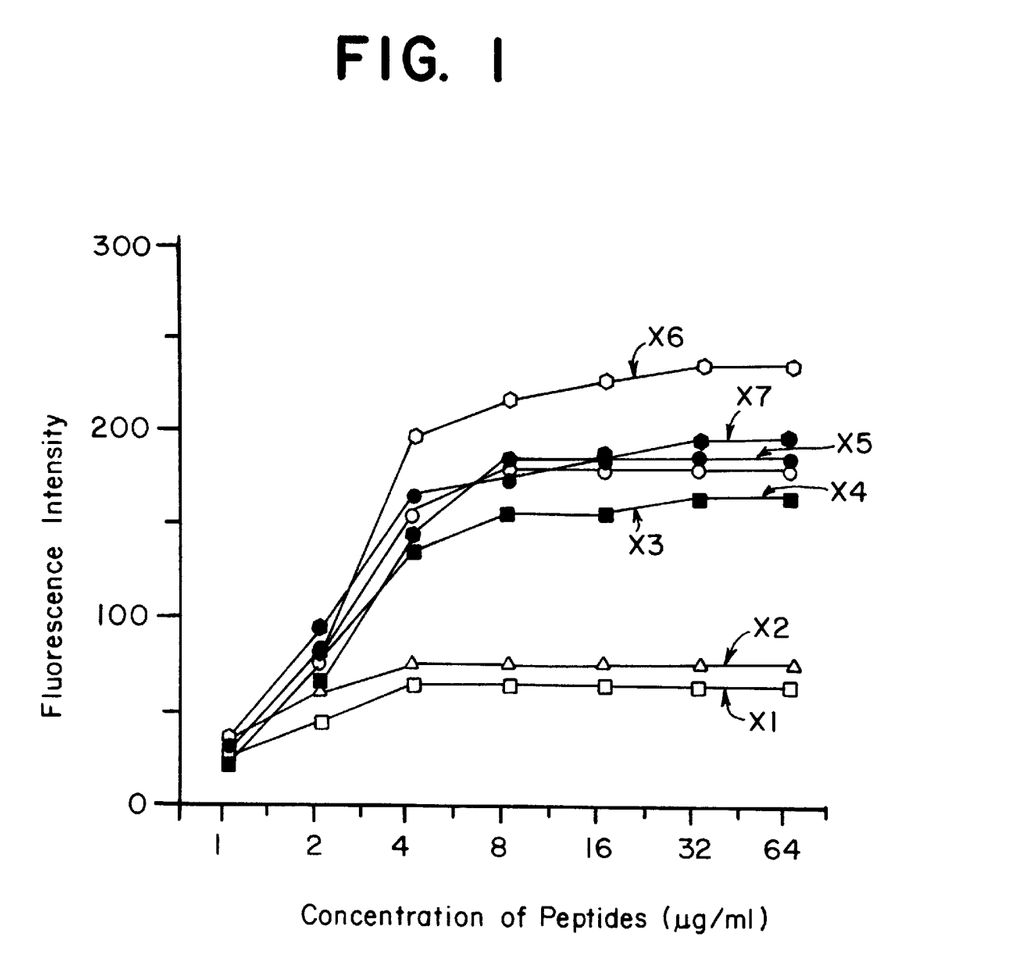
FIG. 1 is a graph showing the change of MHC Class I molecules expressed at the surface of T2 cell, which is represented as strength of fluorescence.

As shown in FIG. 1, it was found that 5 peptides such as X3, X4, X5, X6 and X7 successfully bind to MHC Class I molecules at the surface of T2 cell. Peptides used in the experiment are disclosed in Table 2 below.

TABLE 2

Amino acid sequences of synthesized peptides

| Synthetic peptide | Position of amino acid sequence | Amino acid sequence* | Number of amino acid |
|---|---|---|---|
| x1 (SEQ ID NO: 6) | 015–023 | VLCLRPVGA | 9 |
| x2 (SEQ ID NO: 7) | 036–044 | TLPSPSSSA | 9 |
| x3 (SEQ ID NO: 1) | 052–060 | HLSLRGLFV | 9 |
| x4 (SEQ ID NO: 2) | 092–100 | VLHKRTLGL | 9 |
| x5 (SEQ ID NO: 3) | 102–110 | AMSTTDLEA | 9 |
| x6 (SEQ ID NO: 4) | 115–123 | CLPKDWEEL | 9 |
| x7 (SEQ ID NO: 5) | 126–134 | EIRLKVFVL | 9 |

*: Amino acid sequences are abbreviated according to the IUPAC-IBU nomenclature system.

T2 cell line employed in the Example has a disorder in intracellular transporting pathway of peptides and does not permit proper binding of MHC Class I molecule with peptide to give rise to unstable molecular structure, which results in low expression of MHC molecule during cultivation at 37° C., normal growth temperature. However, when T2 cells are cultivated in a medium containing peptides which can bind to MHC molecules, the peptides bind to MHC molecules at the surface of T2 cell to increase stability of MHC molecules, which results in increase in expression of MHC molecule. Based on the knowledge, binding of a specific peptide to MHC molecule at the surface of T2 cell can be analyzed by determining degree of binding of BB7.2 antibody to the cell surface.

EXAMPLE 3

Determination of Recognition of a Peptide by CTL

Binding of a certain peptide to a MHC molecule cannot prove recognition of the peptide by CTL. Accordingly, further experiment was carried out in order to investigate whether the peptides used for determination of binding to MHC molecules in Example 2 are really recognized by CTL which can recognize HBV within human body.

Figure 2:
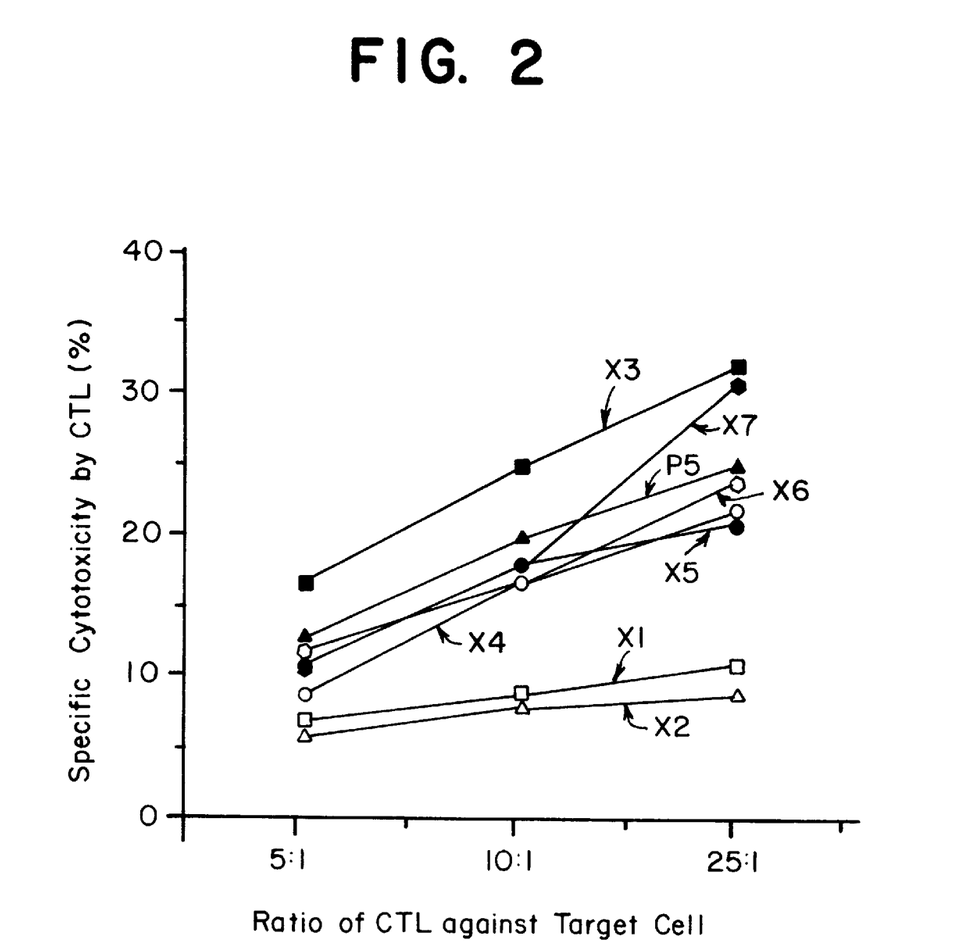
FIG. 2 is a graph showing cytotoxicity of CTL against T2 cell.

That is, blood positive to anti-HBV antibody(value obtained by ELISA: 1.0 or more) is collected from common blood donors, and centrifuged to harvest blood cells. The said peptides added in a concentration of 10 μg/ml to leukocytes remained after removing red blood cells from the blood cells, and incubated at 37° C. in a $CO_2$ incubator maintained to contain 5% $CO_2$. At 2 days after culture, 10 unit of interleukin-2 was added to the culture medium and the cells were further cultivated for 3 days. Then, blood cells having the same MHC were inactivated by mitomycin C and added to the culture medium as stimulating cells. And the peptides and interleukin-2 were added to the medium and the cells were further cultivated for 7 days. Then, it was determined whether the blood cells recognize and destruct T2 cells having a certain peptide at their surface, and the results were shown in Table 3 below and FIG. 2, respectively.

TABLE 3

Cytotoxicity of peptide-specific T cell against target cell sensitized by synthesized peptides

| | Specific cytotoxicity by CTL (%) | | |
|---|---|---|---|
| Synthetic peptide | 5:1* | 10:1* | 25:1* |
| x1 | 6 | 11 | 15 |
| x2 | 5 | 10 | 11 |
| x3 | 10 | 17 | 20 |
| x4 | 8 | 16 | 21 |
| x5 | 16 | 24 | 31 |
| x6 | 11 | 16 | 23 |
| x7 | 12 | 19 | 24 |
| p 5 | 10 | 17 | 30 |
| control | 5 | 13 | 16 |

*: Ratio of CTL against target cell

Destruction of T2 cell by cultured blood cell was determined as followings: 100 μg/ml of a peptide was added to T2 cells and reacted at 37° C. for 3 hours. Then, the cells were washed sufficiently to remove unreacted peptides, added with radioactive sodium chromate($Cr^{51}$), and reacted at 37° C. for 2 hours in a $CO_2$ incubator. And then, they were washed with RPMI medium sufficiently to remove unreacted sodium chromate, mixed with blood cells washed with PBS in a certain ratio, and reacted at 37° C. for 4 hours in a $CO_2$ incubator. The resultant medium was collected and measured for intensity of gamma ray to determine cytotoxicity of the blood cells against T2 cell, i.e., target cell.

As can be seen in Table 3 above, it was found that X3, X4, X5, X6, X7 and P5, are recognized by cultured blood cells; where P5 is a known peptide playing as a role of a positive control(see: Nayersina, R. et al., J. immunol., 150:4659–4671(1993)), which demonstrates that the experimental methods employed in the present Example are suitable.

EXAMPLE 4

Preparation of pH-sensitive Liposomes Comprising Peptide Antigens

Phospholipid consisting of POPE/CHOH(7:3 in a molar ratio) or POPE/PE/CHOH(3.5:3.5:3 in a molar ratio) was added into a glass vial and dissolved in an organic solvent. Then, nitrogen gas was introduced into the vial to form lipid thin film within the vial. And then, buffer(pH 8.0) containing peptides to be encapsulated was added to the lipid film for sufficient hydration, and stirred vigorously to prepare multilamellar vesicle("MLV"), from which small unilamellar vesicle("SUV") was prepared by sonicating the MLV. The SUV thus obtained was incubated at a room temperature for 2 to 12 hours, and rapid freezing of the SUV using liquid nitrogen and slow thawing at a room temperature were repeated 3 or 4 times to prepare liposomes comprising peptides. Thus, the liposomes were finally prepared by mixing peptide and phospholipid in a molar ratio of 1:20. In this connection, the peptides used were peptide antigens which were derived from HBV X protein and can induce CTL response by binding to MHC Class I molecules(see: Table 1 above).

Physical stability and pH-sensitivity of the liposomes thus obtained were investigated as followings, which showed low destruction of the liposome by ethanol treatment and very low leakage of liposomal contents, compared with the conventional pH-sensitive liposomes:

(1) Determination of Physical Stability

Physical stability of the liposomes thus prepared was determined by measuring change in turbidity when ethanol was added to the liposome solution. Since ethanol treatment destroys liposome, which results in decrease in turbidity, stability of liposome was determined by measuring change in absorbance at 400 nm. As a result, it was found that liposomes comprising the peptides of the invention have higher physical stability than the conventional pH-sensitive liposomes.

(2) Determination of pH-sensitivity 12.5 mM 8-aminonaphtylene-1,3,6-trisulfonic acid disodium salt(ANTS), 45 mM p-xylene bis(pyridinum)bromide (DPX), 68 mM NaCl and 10 mM HEPES buffer solution (pH 8.0) were encapsulated into the liposomes comprising the peptides, and ANTS and DPX which were not encapsulated were removed by using Sephadex G-50 column(1× 20 cm) to collect only liposome solution. Concentration of phospholipid within liposomes was determined according to Vaskovsky's method(see: Vaskovsky, V. E., Kostetsky, E. Y. and Vasendin, I. M., J. Chromatogr., 114:129(1975)).

In the experiment for determination of pH-sensitivity, intensity of fluorescence of liposome solution passing through the column is defined as '0% leakage' and that of liposome solution destroyed by Triton X-100 is defined as '100% leakage'. Concentrated liposome(30 $\mu$M) was added to 2 ml of buffer solution having respective pH value (7.5, 6.9, 6.4, 5.9, 5.4, 4.9 and 4.5), and left to stand at 37° C. for 30 minutes. Then, pH-sensitivity was determined by measuring fluorescence. In this connection, fluorescence was measured at 360 nm of excitation wavelength and 545 nm of emission wavelength, using spectrofluorometer(FP-777, JASCO, Japan).

As a result, it was revealed that the liposomes comprising the peptides of the invention showed lower leakage of liposomal contents(~20%) than the conventional pH-sensitive liposomes used as a control (~80%).

EXAMPLE 5

Induction of Cellular Immunity by pH-sensitive Liposomes Comprising Peptides

In order to investigate whether pH-sensitive liposome as a carrier of peptides can induce CTL response specific to the virus from which the peptides are derived, pH-sensitive liposomes encapsulating synthetic peptides were prepared and cytotoxicity study were carried out in a serial manner. Since the cellular immunity of the pepitides which can bind HLA-A2, a human MHC class I molecule should be investigated employing human body, indirect experiment employing the peptides derived HIV and HCV proteins which can bind mouse MHC Class I molecule(see: Table 4 below), was carried out. In this regard, the pH-sensitive liposome comprising the peptides were obtained employing the phospholipid composition consisting of POPE/CHOH(7:3 in a molar ratio). Then, mice were immunized with the liposomes, T lymphocytes were isolated from the mice, and cytotoxicity of the T lymphocytes after recognition of target cells labelled with $Cr^{51}$ was determined.

TABLE 4

Amino acid sequences(*) of peptides recognized by neutralized antibody and mouse CTL, which are derived from HIV and HCV proteins

| Synthetic peptide | Amino acid sequence | Number of amino acids and origin |
| --- | --- | --- |
| R15K[1] (SEQ ID NO: 8) | RIQRGPGRAFVTIGK | 15 mer, HIV |
| T26K[2] (SEQ ID NO: 9) | TRPNNNTRKRIRIQRGPGRAFV TIGK | 26 mer, HIV |
| D8L[3] (SEQ ID NO: 10) | DLMGYIPL | 8 mer, HCV |

*: Amino acid sequences are abbreviated according to the IUPAC-IBU nomenclature system.
[1]: amino acid sequence of HIV gp120 at position of 315–329
[2]: amino acid sequence of HIV gp120 at position of 304–329
[3]: amino acid sequence of HCV core protein at position of 131–138

In case of HIV, Balb/C mouse was immunized with pH-sensitive liposomes comprising R15K or T26K, and at 4 weeks after booster immunization, its spleen was dissected and homogenized in 2 ml of RPMI cell culture medium using a homogenizer. 2 ml of the homogenate thus obtained was added to 2 ml of ficoll and centrifuged at 1,500 rpm for 30 minutes. T lymphocytes located between ficoll and the cell culture medium were separated, added to 15 ml of RPMI-10 cell culture medium, centrifuged at 1,000 rpm, and washed three times with the RPMI-10 medium. The T lymphocytes were diluted to a cell concentration of $5 \times 10^6$/ml into a 24 well-plate, and the immunized peptide antigen was added to a final concentration of 2 $\mu$M. Then, the cells were cultured at 37° C. for 3 days in a $CO_2$ incubator containing 5% $CO_2$ and used as effector cells. In case of HCV, 5 week-old C57BL/6 mouse was immunized with liposomes comprising DBL peptide antigen, and T lymphocytes were isolated in the same manner as above and used as effector cells. On the other hand, p815 cell(ATCC TIB64) having MHC Class I same as that of Balb/C mouse was used as a target cell in case of HIV, and RMA cell(see: Hosken, N. A. and Bevan, M. J., J. Exp. Med., 175:719(1992)) or EL4 cell(ATCC TIB39) having MHC Class I same as that of C57BL/6 mouse was used as a target cell in case of HCV.

100 $\mu$M of the immunized peptide was added to the respective target cells, reacted at 37° C. for 16 hours, and washed twice with RPMI cell culture medium. Then, radioactive sodium chromate($Cr^{51}$) was added to the cells and reacted at 37° C. for 2 hours in a $CO_2$ incubator. After reaction, the cells were washed sufficiently with RPMI cell culture medium to remove unreacted sodium chromate, mixed with effector cells washed with phosphate buffer solution in various mixing ratios shown in table 5 below, and reacted at 37° C. for 4 hours in a $CO_2$ incubator. The resultant medium was collected and measured for the intensity of gamma ray to determine cytotoxicity of effector cells against target cells(see: Table 5).

As can be seen in Table 5, it was revealed that effector cells isolated from spleens of mice immunized with R15K, T26K and D8L peptide antigens can recognize and kill target cells. Moreover, it was found that when mice were immunized with peptide antigens inducing CTL response, employing pH-sensitive liposomes, cellular immunity which produce CTLs specific to the virus could be induced.

TABLE 5

Cytotoxicity of peptide-sepcific CTL against target cell

| Peptide antigen | Specific cytotoxicity by CTL (%) | | |
|---|---|---|---|
| | 1:10* | 1:20* | 1:30* |
| R15K | 7.5 | 15 | 25 |
| T26K | 55 | 80 | 87 |
| D8L | 5.5 | 18 | 30 |

*: A ratio of target cell:effector cell

From the indirect experiments on the induction of cellular immunity which were carried out by employing the pH-sensitive liposomes comprising the peptides derived from HIV and HCV proteins, it was clearly demonstrated that: the liposomes comprising the peptide antigens derived from HBV X protein can induce cellular immunity, which in turn induce human CTL response, since the peptide antigens derived from HBV X protein can nduce CTL response in human(see- Example 3) and the pH-sensitive liposomes comprising the peptides can also induce CTL response specific to the virus from which the peptides are derived.

EXAMPLE 6

Eradication of Human Hepatocellular Carcinoma by HBx Specific T Cell

Figure 3A:
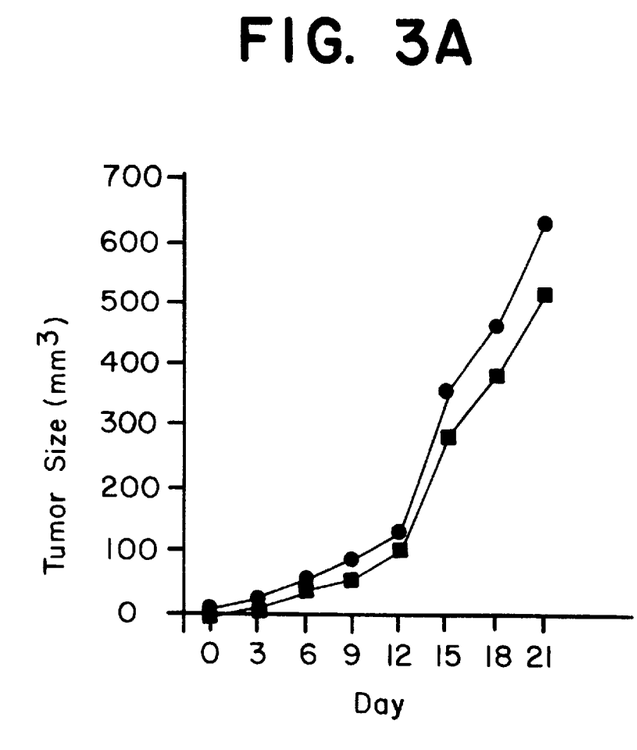
FIG. 3(A) is a graph showing tumorigenicity of nude mice challenged with human hepatocellular carcinoma.
Figure 3B:
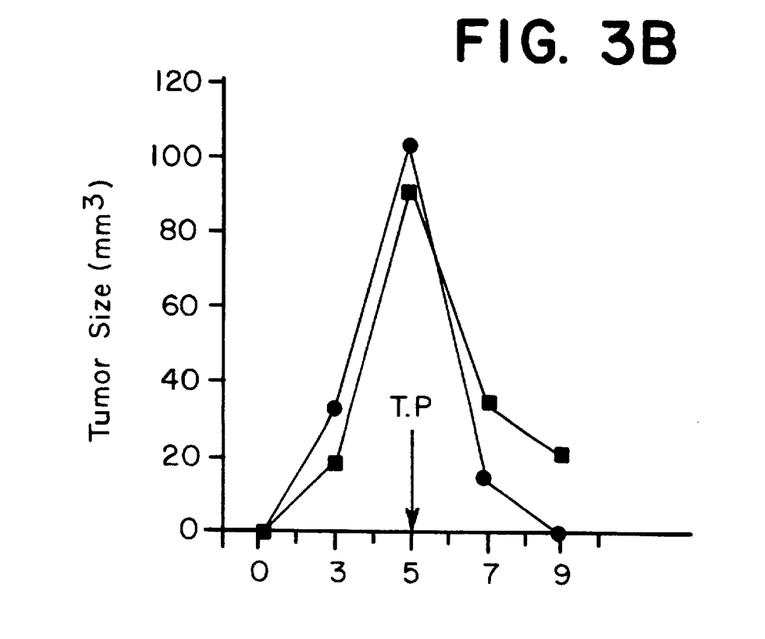
FIG. 3(B) is a graph showing tumor eradication of the nude mice after treatment of CTLs stimulated with peptide antigens derived from HBV X protein.

Tumor eradication by CTLs which were stimulated with peptide antigens derived from HBV X protein(i.e., HBx peptide) was investigated as followings: Human hepatocellular carcinoma cells were subcutaneously challenged to Balb/C based nude mice with different cell numbers of $1\times10^7$ to $2\times10^7$, and tumorigenicity test was conducted on the nude mice. After 3 days, tumors could be detected and after 5 days, adoptive transfer of CTLs stimulated with HBx peptide to the vein in tail of mouse in which tumors had been established was carried out with $1.5\times10^8$ cell numbers(see: FIG. 3(A)). As a result, it was demonstrated that the tumor size began to decrease post treatment 2 days and tumors were completely eradicated on 4th day after the treatment (see: FIG. 3(B)). In FIGS. 3(A) and 3(B), (—●—) and (—▲—) represent challenges of $2\times10^7$ and $1\times10^6$ of tumor cells, respectively, and T.P. represents treatment point of CTLs.

As clearly illustrated and demonstrated as aboves, the present invention provides pH-sensitive liposomes which comprise peptide groups corresponding to epitopes of antigens derived from HBV X protein which induce CTL against the virus or immunological tolerance to the virus, so that cellular immunity against HBV can be induced. Since the peptide antigens derived from X protein such as X3, X4, X5, X6 and X7 activate CTL which can recognize HBV antigens present in human body, and can also be recognized by the CTL, the said pH-sensitive liposomes comprising peptide antigens derived from HBV X protein can be used for the development of proposed therapeutic agents for the prevention and treatment of HBV-associated diseases.

What is claimed is:

1. A synthetic peptide derived from X protein of hepatitis B virus which is recognized by cytotoxic T lymphocytes to be cytotoxic against hepatitis B virus, whose amino acid sequence consists of (SEQ ID NO:1):

His-Leu-Ser-Leu-Arg-Gly-Leu-Phe-Val.

2. A synthetic peptide derived from X protein of hepatitis B virus which is recognized by cytotoxic T lymphocytes to be cytotoxic against hepatitis B virus, whose amino acid sequence consists of (SEQ ID NO:3):

Ala-Met-Ser-Thr-Thr-Asp-Leu-Glu-Ala.

* * * * *